(12) United States Patent
Cohen

(10) Patent No.: US 6,540,753 B2
(45) Date of Patent: Apr. 1, 2003

(54) INSTRUMENTATION FOR IMPLANT INSERTION

(75) Inventor: Herb Cohen, Shelton, CT (US)

(73) Assignee: Howmedica Osteonics Corp., Allendale, NJ (US)

(*) Notice: Subject to any disclaimer, the term of this patent is extended or adjusted under 35 U.S.C. 154(b) by 46 days.

(21) Appl. No.: 09/815,500

(22) Filed: Mar. 23, 2001

(65) Prior Publication Data

US 2002/0138079 A1 Sep. 26, 2002

(51) Int. Cl.$^7$ ................................ A61B 17/56
(52) U.S. Cl. .................... 606/99; 606/90; 600/201; 600/221
(58) Field of Search ............... 606/61, 99, 96, 606/90, 105; 600/201, 210, 226, 235, 221

(56) References Cited

U.S. PATENT DOCUMENTS

| | | |
|---|---|---|
| 3,486,505 A | 12/1969 | Morrison |
| 3,719,186 A | 3/1973 | Merig, Jr. |
| 3,848,601 A | 11/1974 | Ma et al. |
| 3,867,932 A | 2/1975 | Huene |
| 4,834,757 A | 5/1989 | Brantigan |
| 4,877,020 A | 10/1989 | Vich |
| 4,878,915 A | 11/1989 | Brantigan |
| 4,961,740 A | 10/1990 | Ray et al. |
| 5,026,373 A | 6/1991 | Ray et al. |
| 5,122,130 A | 6/1992 | Keller |
| 5,431,658 A | 7/1995 | Moskovich |
| 5,445,639 A | 8/1995 | Kuslich et al. |
| 5,484,437 A | 1/1996 | Michelson |
| 5,489,307 A | 2/1996 | Kuslich et al. |
| 5,505,732 A | 4/1996 | Michelson |
| D374,283 S | 10/1996 | Michelson |
| 5,562,736 A | 10/1996 | Ray et al. |
| 5,571,109 A | 11/1996 | Bertagnoli |
| 5,700,291 A | 12/1997 | Kuslich et al. |
| 5,720,748 A | 2/1998 | Kuslich et al. |
| D397,436 S | 8/1998 | Michelson |
| 5,797,909 A | 8/1998 | Michelson |
| RE36,020 E | * 12/1998 | Moore et al. ............... 606/144 |
| 6,004,326 A | * 12/1999 | Castro et al. ................. 606/99 |
| 6,033,405 A | 3/2000 | Winslow et al. |
| 6,042,582 A | 3/2000 | Ray |
| 6,059,790 A | 5/2000 | Sand et al. |
| 6,063,088 A | 5/2000 | Winslow |
| 6,080,155 A | 6/2000 | Michelson |
| 6,081,741 A | * 6/2000 | Hollis ....................... 600/424 |
| 6,083,225 A | 7/2000 | Winslow et al. |
| 6,096,038 A | 8/2000 | Michelson |
| 6,113,602 A | 9/2000 | Sand |
| 6,120,503 A | 9/2000 | Michelson |
| 6,224,607 B1 | * 5/2001 | Michelson ................... 606/96 |
| 6,241,541 B1 | * 6/2001 | Hida .......................... 439/188 |

FOREIGN PATENT DOCUMENTS

| | | |
|---|---|---|
| DE | 8703 654 U | 7/1987 |
| WO | WO 93/22975 | 11/1993 |
| WO | WO 99/52453 | 10/1999 |

* cited by examiner

Primary Examiner—Kevin Shaver
Assistant Examiner—Michael B. Priddy
(74) Attorney, Agent, or Firm—Lerner, David, Littenberg, Krumholz & Mentlik, LLP

(57) ABSTRACT

An implant insertion apparatus for guiding surgical instrumentation and facilitating insertion of surgical implants into an intervertebral space, including a retractor having an internal opening for introduction of a surgical instrument and positionable with respect to adjacent vertebrae in the intervertebral space, and a guide bar mounted to the retractor. The guide bar includes a longitudinal guide shaft dimensioned to guide introduction of surgical instrumentation through the internal opening of the retractor. The apparatus further includes a guide member mounted to the surgical instrument for providing the guidance thereof.

13 Claims, 6 Drawing Sheets

INSTRUMENTATION FOR IMPLANT INSERTION

BACKGROUND

1. Technical Field

The present disclosure generally relates to a method and associated instrumentation for implant insertion and, in particular, to a method and instrumentation for insertion of spinal implants to facilitate fusion of adjacent vertebral bodies.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. Some implants are particularly configured with cavities and bores to facilitate bony in-growth and enhance anchoring of the implant at the insertion site. Implants in the form of fusion cages having internal cavities to receive bone growth stimulation materials such as bone chips and fragments are disclosed, for example, in U.S. Pat. No. 4,501,269 to Bagby; and U.S. Pat. No. 4,961,740 to Ray et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating direct fusion of the vertebrae while maintaining a pre-defined intervertebral space. This fusion may be accomplished by the insertion of one or more of the specialized implants as discussed above and also discussed in commonly assigned U.S. Pat. No. 5,026,373, the contents of which are incorporated herein by reference.

Both anterior (transabdorninal) and posterior surgical approaches are used for interbody fusions of the lumbar spine. Fusions in the cervical area of the spine are primarily performed using a posterior approach. Typically, an implant such as a plug, dowel, prosthesis or cage is inserted into a preformed cavity inside the interbody, interdiscal space. Since it is desirable in these procedures to promote a "bone to bone" bridge, connective tissue and at least a portion of the distal tissue is removed. Preferably, relatively deep cuts are made in the adjacent bones in order to penetrate into the softer, more vascularized cancellous region to facilitate bone growth across the implant.

SUMMARY OF THE INVENTION

One of the more critical tasks performed in the insertion of a surgical fusion implant, particularly, in intervertebral spinal fusion, is the formation of the implant receiving cavity or bore between/within the adjacent vertebrae. More particularly, the drilled bore must be equally centered within the intervertebral space and preferably parallel to the vertebral end plates to ensure removal of equal portions of bone from the adjacent vertebrae throughout the length of the cut and subsequent appropriate seating of the implant relative to the vertebral bodies. In addition, the length of the cut by the drill must be accurate depending upon the particular surgical needs for the patient and/or the length of the implant to be inserted.

Accordingly, the present invention is directed to provide an improved instrumentation and associated method to facilitate the introduction of fusion implants, which ensures simplified and effective procedures for the implantation.

In accordance with the present disclosure, an implant insertion apparatus includes a retractor having an internal opening for introduction of surgical instruments therethrough. The retractor is positionable across an intervertebral space with respect to the adjacent vertebrae to maintain the adjacent vertebrae at a predetermined spaced relation. The insertion apparatus further includes an elongated guide bar mounted to the retractor and defining a longitudinal guide shaft to guide introduction of the surgical instrument through the opening of the retractor. The surgical instrument is advanceable along the guide bar into the intervertebral space.

The present disclosure is also directed to a method for performing a surgical procedure with the implant insertion apparatus.

BRIEF DESCRIPTION OF THE DRAWINGS

Preferred embodiments of the disclosure are described hereinbelow with reference to the drawings wherein:

FIG. 3 is a perspective view of an alternate embodiment of the implant insertion apparatus, illustrating a retractor and guide bar having mounting structure for releasable connection there-between;

DETAILED DESCRIPTION OF THE PREFERRED EMBODIMENT(S)

The preferred embodiments of the method and instrumentation disclosed herein are discussed in terms of orthopedic spinal fusion procedures and instrumentation. It is also envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of each instrument utilized in performing a spinal fusion followed by a description of the preferred method for spinal fusion utilizing the instrumentation in accordance with the present disclosure.

In the discussion which follows, the term "proximal", as is traditional, will refer to the portion of the structure which is closer to the operator, while the term "distal" will refer to the portion which is further from the operator.

Figure 1:
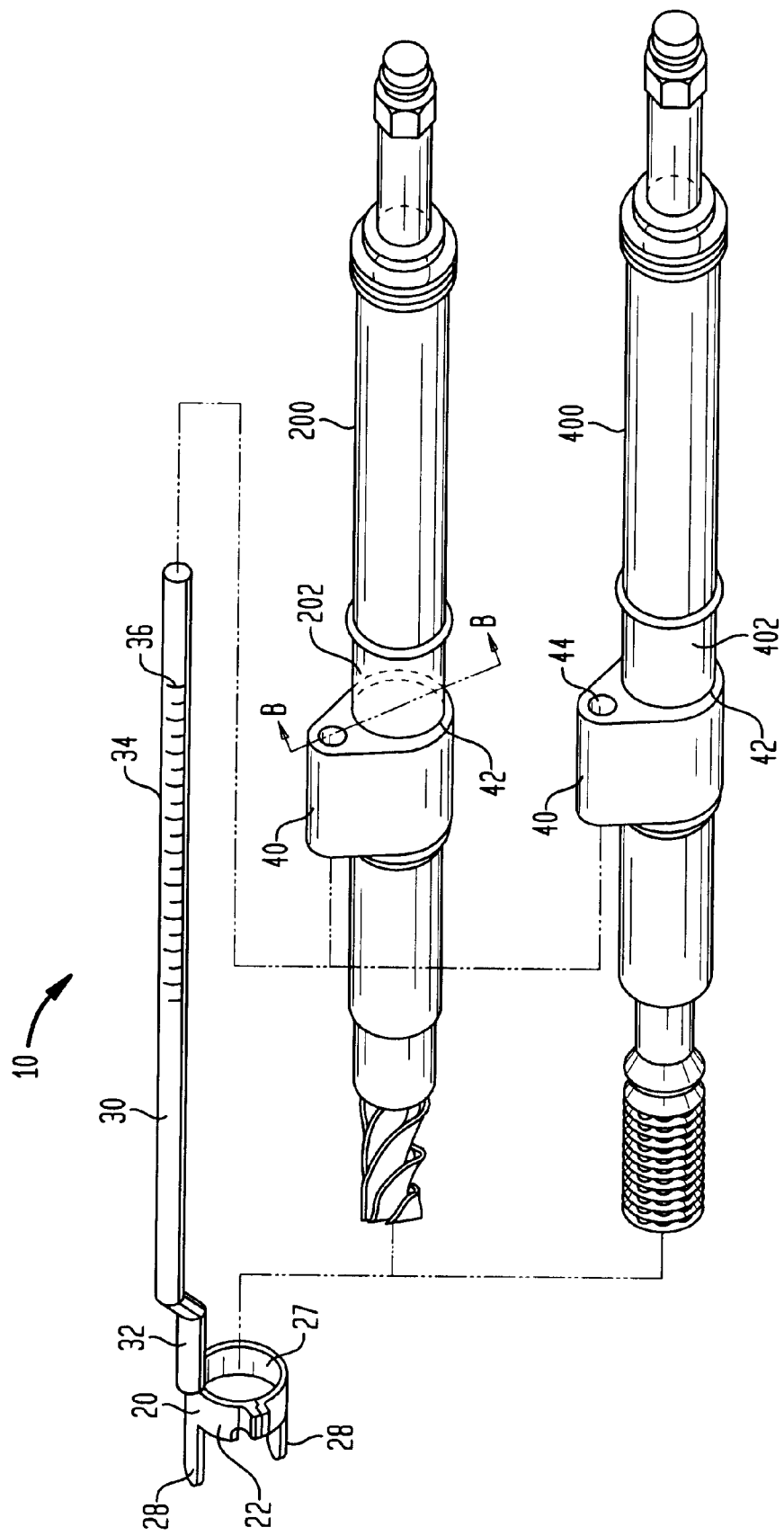
FIG. 1 is a perspective view of an implant insertion apparatus constructed in accordance with the present invention, including a retractor, guide bar and guide member mounted to surgical instruments (e.g., a surgical drill and implant insertion tool)

Referring now to FIG. 1 which illustrates in perspective view an implant insertion system constructed according to the principles of the present disclosure, implant insertion apparatus 10 includes retractor 20 and guide bar 30. The system further includes guide member or attachment 40 mounted to the desired surgical instruments, such as surgical drill 200 and implant insertion tool 400. The insertion apparatus 10 is particularly contemplated for distracting adjacent bony structures, e.g., adjacent opposed vertebral bodies, for providing an opening to facilitate insertion of surgical instrumentation, and for ensuring proper alignment of the instrumentation and accurate insertion of the implant. Although described for spinal procedures, it is envisioned that insertion apparatus 10 may also be utilized to distract other structures as well including joints, ligaments, etc.

Retractor 20 includes base portion 22 having a proximal end portion and a distal end portion and longitudinal opening 27 extending therethrough to permit introduction of surgical instruments. Retractor 20 further includes first and second spacer arms 28 extending longitudinally from the distal end of base portion 22. Each spacer arm 28 defines a first vertebra supporting surface 28a to contact a first vertebra and a second vertebra supporting surface 28b to contact a second vertebra with the surfaces 28a and 28b preferably being in general parallel relation to each other. The height "h" of each arm 28 ranges from about 0.3 to 0.4 inches and more preferably from about 0.28 to about 0.35 inches. One skilled in the art will readily appreciate that this dimension can be varied as needed depending upon the procedure. Each arm 28 further includes tapered end portions 28c defining a generally V-shaped configuration. End portions 28c facilitate insertion of the arms 28 within the surgical site, e.g. within the intervertebral space.

Referring still to FIG. 1, the guide bar 30 includes a distal mounting portion 32 connected to the retractor 20 and a longitudinal guide shaft 34. The guide shaft 34 of the guide bar 30 is dimensioned to guide surgical instruments into the opening 27 of the retractor 20. The guide shaft 34 may have dovetail cross-sectional area along its shaft to prevent any lateral movement of surgical instruments. The guide shaft 34 includes depth markings 36 for providing indication of insertion depth of the surgical instruments into the intervertebral space defined between adjacent vertebrae.

Figure 2:
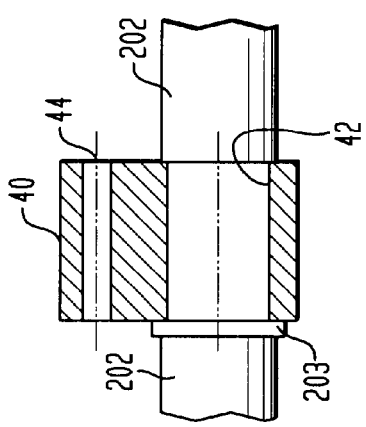
FIG. 2 is a partial cross-sectional view illustrating a guide member mounted to a surgical instrument, which is taken along the lines B—B in FIG. 1.

Surgical instruments to be used with the implant insertion apparatus, including surgical drill 200 and implant insertion tool 400, are adapted to mount guide member 40 respectively in their mounting portions 202 and 402. Guide member 40 includes cylindrical openings 42, 44 extended longitudinally through its proximal and distal end surfaces. The opening 42 is dimensioned to rotatably receive shafts 202 and 402. However, as shown in FIG. 2, the longitudinal movement of the guide member 40 is preferably prevented by having a larger cross-sectional dimension at the proximal end portion of the shafts 202 and 402, along with collar 203 fixed at a distal portion of the shafts 202 and 402. The other opening 44 is dimensioned to slidably receive the guide shaft 34. Similar to the guide shaft 34, the opening 44 may have a matching dovetail cross-sectional area to prevent lateral movement of the guide member 40 while permitting sliding movement there-between. The two openings 42 and 44, along with the shaft 34, are dimensioned to accurately guide the surgical instruments into the opening 27 of the retractor 20, and the longitudinal center axes of two openings 42 and 44 are parallel to each other.

Figure 3:
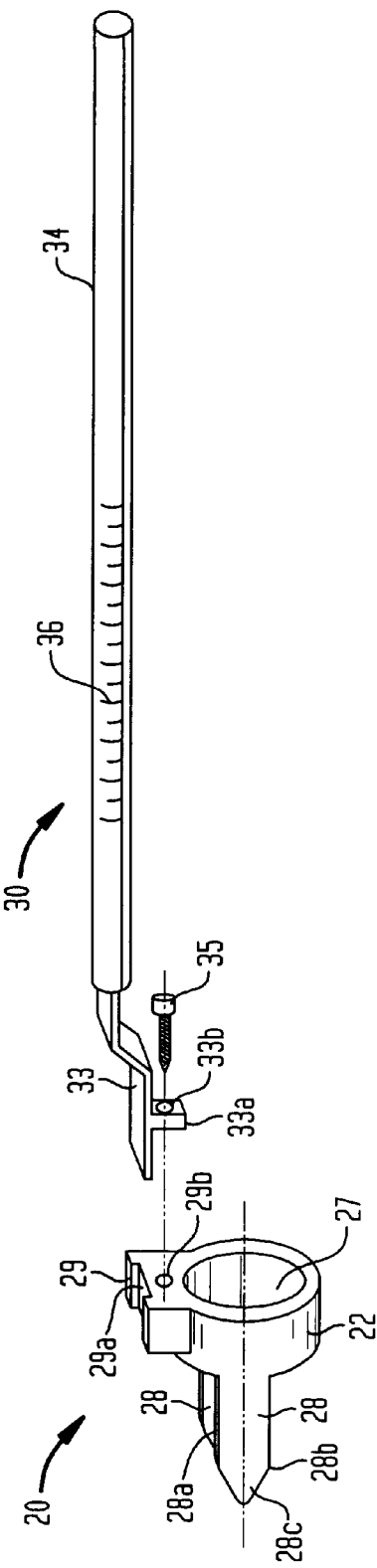

Referring now to FIG. 3 illustrating an alternative embodiment to the implant insertion apparatus of FIG. 1, retractor 20 includes mounting block 29 around the base portion 22. The block 29 preferably includes a longitudinal slot 29a extending in parallel relation with the axis of opening 27 of the retractor 20. The block 29 further includes a threaded hole 29b built longitudinally at its proximal end. Guide bar 30 includes a mounting portion 33 at its distal end and a longitudinal guide shaft 34 at its proximal end. The distal end of the mounting portion 33 is dimensioned to slidably fit within the slot 29a of the block 29. Mounting portion 33 includes a transverse portion 33a extended transversely from a distal portion thereof, which has a hole 33b for receiving a screw 35. Upon locking the screw 35 into the holes 33b and 29b, the guide bar 30 may be releasably mounted to the retractor 20. As is described above in association with FIG. 1, guide shaft 34 is likewise dimensioned to guide surgical instruments into the opening 27 of the retractor 20.

Figure 4:
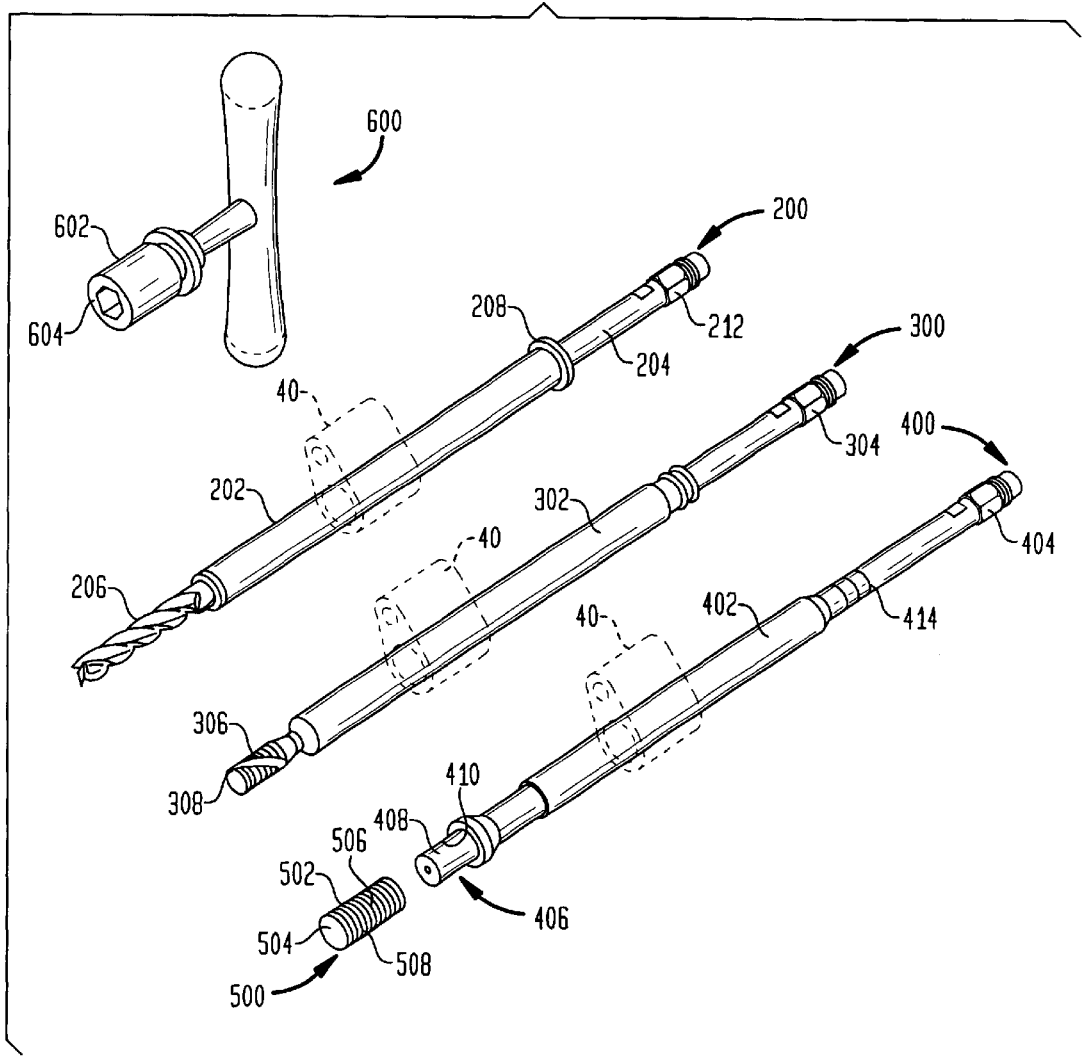
FIG. 4 is a perspective view of a surgical kit utilized for insertion of a fusion implant including, from bottom to top, an implant insertion instrument and fusion implant, a tap instrument, a drill instrument and a T-shaped handle.

Referring now to FIG. 4, the various instruments contemplated for use together with the implant insertion apparatus in the spinal fusion procedure are illustrated, including surgical drill 200, surgical tap instrument 300, implant insertion instrument 400 with implant 500 and T-shaped handle 600. Drill instrument 200 includes drill shaft 202, extension shaft 204 and drill bit 206 mounted at the distal end of the drill shaft. Drill shaft 202 includes a hexagonal-shaped head 212 at its proximal end to mount T-handle 600. As described above in association with FIGS. 1–2, drill shaft 202 is adapted to mount guide member 40 for providing accurate guidance of the drill bit 206 into the opening 27 of the retractor 20.

Tap instrument 300 is utilized for performing an internal thread within the drilled bore formed by the drill instrument. Tap instrument 300 includes elongated member 302 having hex head 304 at its proximal end to engage T-shaped handle 600. Tap instrument 300 further includes distal tapping threaded portion 306. Distal tapping portion 306 includes a plurality of conveyance channels (one is shown) 308 extending longitudinally through the cutting thread. Each conveyance channel 308 has a directional component parallel to the longitudinal axis and a directional component transverse to the longitudinal axis. Each conveyance channel 308 encompasses approximately an arc of about ⅓ the outer circumference of the tapping portion 306 Conveyance channels 308 are each dimensioned to receive bone material deburred by the cutting edges during the tapping procedure and to continually transmit the bone material proximally through the channel to avoid undesired material build up at the tapping site. In this manner, tapping instrument 300 may be used to completely tap the internal thread within the bore without interruption of the tapping procedure. The shaft 302 may be adapted to mount guide member 40, similarly to the drill shaft 202. It should be noted that the tap need not be used if a self-tapping implant is utilized.

Implant insertion instrument 400 includes elongated member 402 having proximal mounting portion 404 to engage T-shaped handle 600 and distal portion 406 which mounts implant 500. Distal portion 406 includes cylindrical mount 408 which is received within the bore of the implant 500 and implant engaging ball 410 which is received within an aperture defined in the wall of the implant 500 to positively fix the implant to the instrument A hand lever 412 is proximally located and is operatively connected to an inner drive member (not shown) disposed within elongated member 402. The hand lever 412 is longitudinally movable to translate the drive member which, in turn, moves through a camming action implant engaging in ball 410 between an outward position in engagement with the implant 500 and an inward position released from the implant 500. The shaft 402 is adapted to mount guide member 40 similarly to the drill shaft 202.

Implant 500 is uniquely designed for use in spinal fusion procedures. This implant 500 is generally disclosed in U.S. Pat. No. 5,026,373 to Ray, the contents of which have been previously incorporated herein by reference, and is commonly referred to as a "fusion cage". Implant or fusion cage 500 includes a cylindrical cage body 502 having an internal cavity or hole for accommodating bone-growth inducing substances. One end 504 of cage body 502 is closed and defines a rounded or bull-nosed configuration to facilitate insertion of the fusion cage relative to one or more bony structures. The other end defines an opening which communicates with the internal cavity. The outer surface of the cage body 502 includes a single continuous thread 506 (preferably V-shaped) having a plurality of raised turns with valleys defined between adjacent turns.

A plurality of perforations 508 are disposed within the threads and extend through the outer surface of the cage body 502 to provide direct communication between the outer surface and internal cavity 504. The perforations 508 permit immediate contact between the bone growth inducing substances within the inner cavity and the bone structure when the cage body 502 is mated to the bone structure, e.g., adjacent vertebrae. An end cap (not shown) may be mountable to the open end of cage body 502 to enclose the bone-growth inducing substances within the interior cavity.

T-shaped handle 600 includes mounting portion 602 defining hexagonal-shaped recess 604 which receives the corresponding structure of drill instrument 200, tap instrument 300 and implant insertion instrument 400.

APPLICATION OF INSTRUMENTATION

The use of the instrumentation in conjunction with the insertion of the fusion cage 500 into an intervertebral space defined between adjacent vertebrae will be described. The subsequent description will be particularly focused on an open posterior spinal fusion procedure. However, it is to be appreciated that an anterior approach or implant insertion approach using two implants in side-by-side relation is contemplated as well.

The intervertebral space is accessed utilizing appropriate instrumentation to expose the posterior vertebral surface. Then, with reference to FIG. 5, the desired-sized vertebral retractor 20 with guide bar 30 connected thereon is placed to an intervertebral space "i". By manipulating guide bar 30, spacer arms 28 of the retractor 20 are inserted within the intervertebral space "i". A standard mallet may be utilized to impact the proximal end of impact cap (not shown) mounted to the opening 27 of the retractor 20 to drive spacer arms 28 into the disc space. Spacer arms 28 are inserted in a manner such that first and second supporting surfaces 28a, 28b of each spacer arm 28 respectively engage the opposed vertebral bodies "$v_1v_2$". Alternatively, if using the implant insertion apparatus of FIG. 3 described above, guide bar 30 may be connected to the retractor 20 after the retractor 20 is positioned into the intervertebral space.

Figure 5:
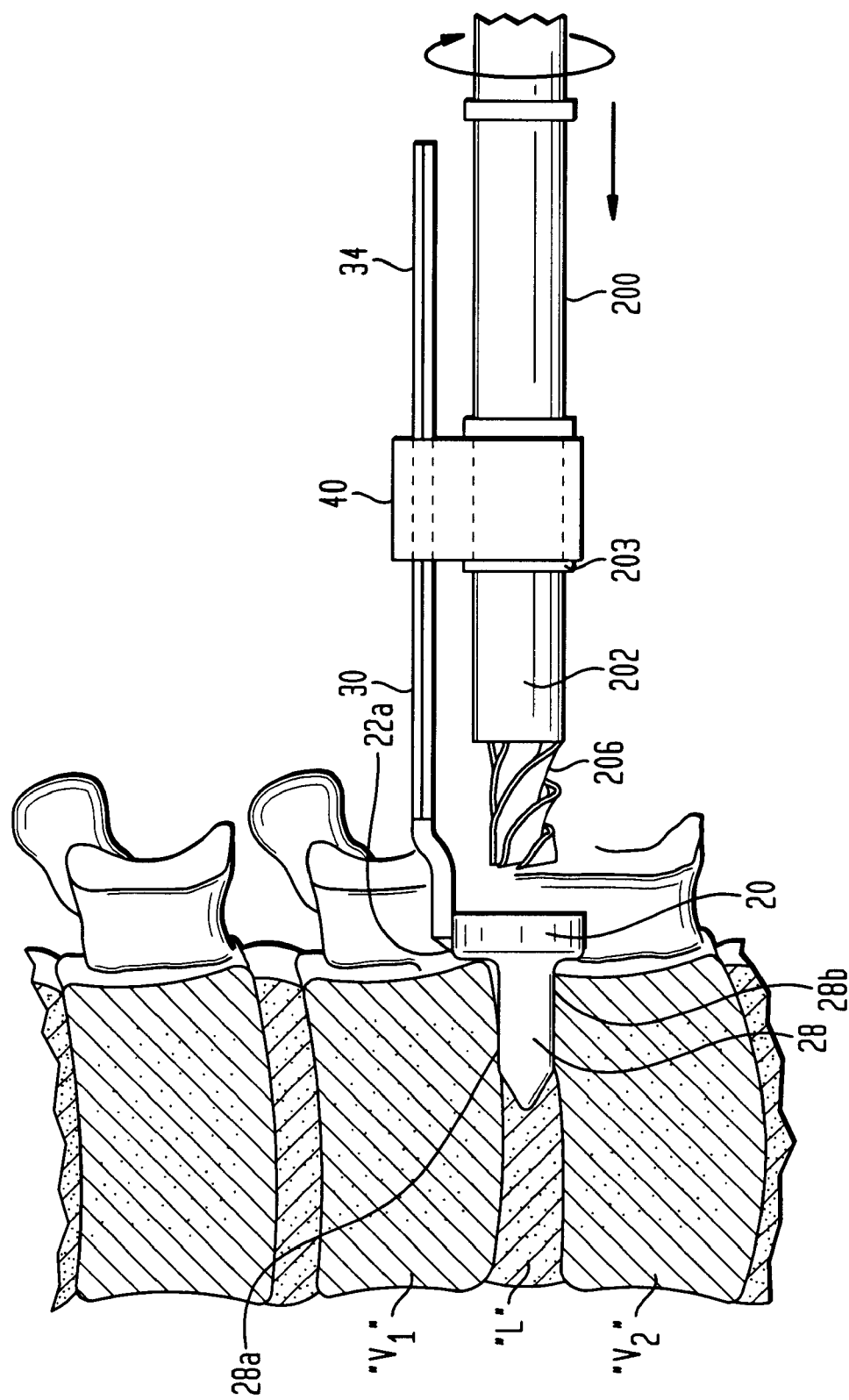
FIG. 5 is a side cross-sectional view of an intervertebral space illustrating positioning of the retractor in the intervertebral space and insertion of the drill instrument guided by the guide member along the shaft of guide bar to drill a bore within the adjacent vertebrae.

With reference still to FIG. 5, surgical drill instrument 200 with guide member 40 mounted thereon is prepared to form a bore space for insertion of the fusion implant into the intervertebral space. Guide member 40 and drill instrument 200 are mounted to the guide bar 30 with the guide shaft 34 inserted into the opening 44 of the guide member 40. Now, with the T-handle mounted to surgical drill instrument 200, the instrument is advanced into the opening 27 of retractor 20 and to the posterior surface of the vertebral bodies "$v_1v_2$" while guided by the guide member 40 which is sliding along the guide shaft 34. Drill 200 is advanced into the intervertebral space "i" by rotating T-handle 600 such that drill bit 206 shears the soft tissue and cuts the bone of the adjacent vertebrae "$v_1v_2$" thereby forming a bore which extends into the adjacent vertebrae "$v_1v_2$", while drilling depth is monitored upon reading depth markings 36 on the guide shaft 34. Once reaching a predetermined depth, as may be facilitated by depth markings 36 on guide shaft 34, drill 20 is stopped and removed from the guide shaft 34.

Now, tap instrument 300 with guide member 40 mounted thereon is prepared and T-handle 600 is attached thereto. Guided by guide member 40 in the same manner as drill instrument described above, tap instrument 300 is introduced adjacent the drilled bore formed in the adjacent vertebrae "$v_1v_2$" by the drill. T-handle 600 is rotated in the appropriate direction while simultaneously applying sufficient downward pressure on the T-handle to advance the tap instrument 300 and promote even purchase into the endplates. Upon advancement of the tap instrument 300, the deburred bone chips collect within conveyance channel 308 of tapping head 306, and are conveyed proximally during rotational movement of the tapping head away from the tapping site. Tap instrument 300 is advanced into the bone until the desired depth has been achieved, which occurs when the distal end of tapping head 308 "bottoms out" on the bone. When tap instrument 300 reaches the appropriate depth, the tap instrument 300 is rotated via T-handle 600 in an opposite direction to back the instrument out of the bone.

Figure 6:
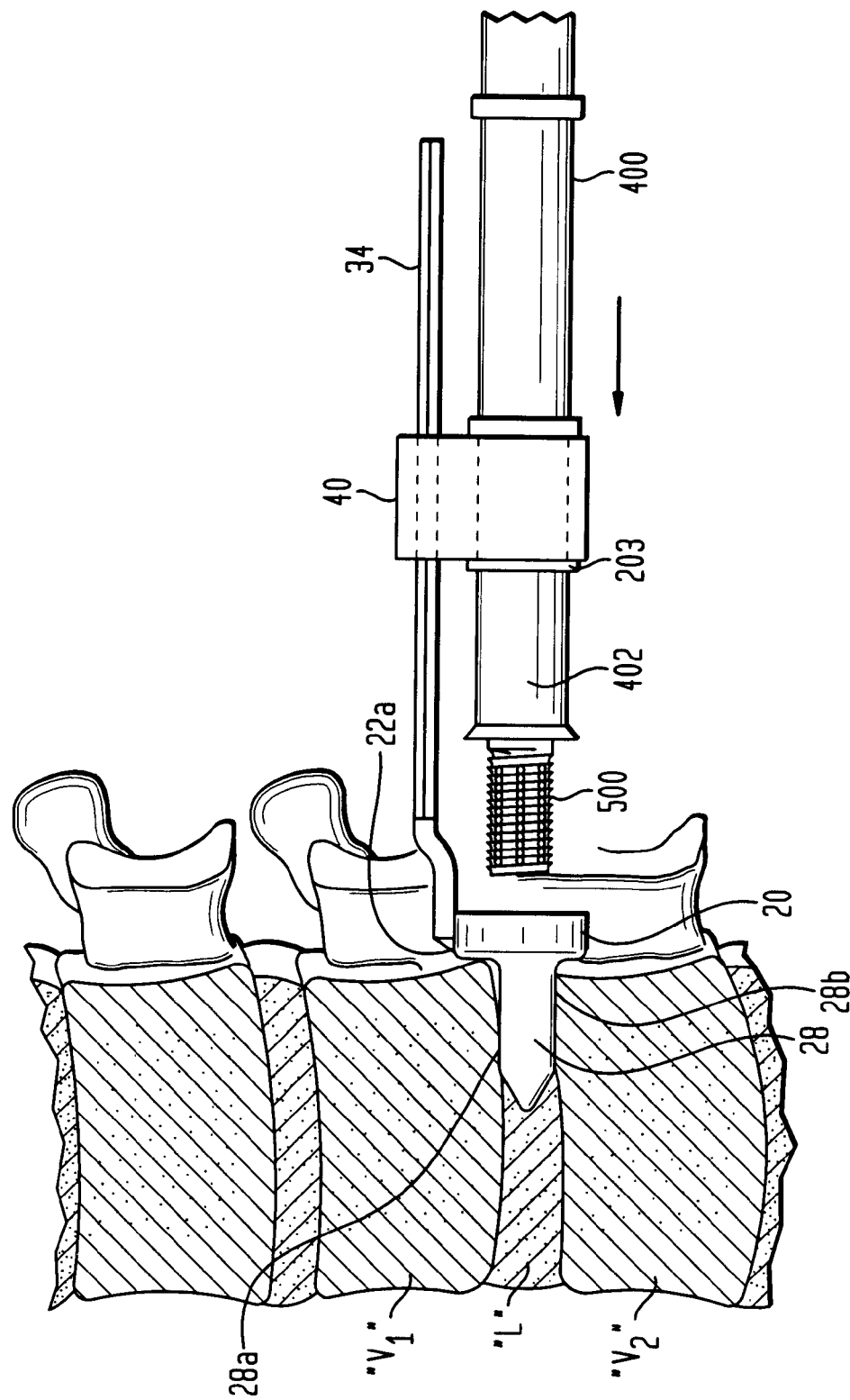
FIG. 6 is a view similar to the view of FIG. 5 illustrating insertion of the implant insertion instrument with mounted implant into the retractor to insert the implant.

With reference now to FIG. 6, implant insertion instrument 400 with guide member 40 mounted thereon is prepared. Cage body 502 is mounted onto the insertion instrument 400 by positioning the cage body 502 onto mounting portion 408 of the instrument to permit mounting ball 410 to engage one of the apertures of the implant 500. This assembly is attached to T-handle 600. Guided by guide member 40 in the same manner as the drill and tap instrument described above, insertion instrument 400 with mounted cage body 502 is inserted into the retractor 20 and the cage body 502 is positioned within the tapped bore by rotating insertion instrument 400 in the appropriate direction. Cage body 502 is advanced until it is completely seated with the bore. Depth indicator 36 (FIGS. 1, 3) on guide shaft 34 assists the surgeon in determining when the cage is in proper position. Insertion instrument 400 is then removed from retractor 20 and guide shaft 34.

At this point in the procedure, bone growth inducing substances may be harvested from, e.g., the iliac crest, and packed into the cage body 502 of implant 500 until the cage body 502 is completely filled with bone growth inducing substances. An end cap may then be mounted to the cage body 202. Retractor 20 is then removed by manipulating the guide bar 30.

Figure 7:
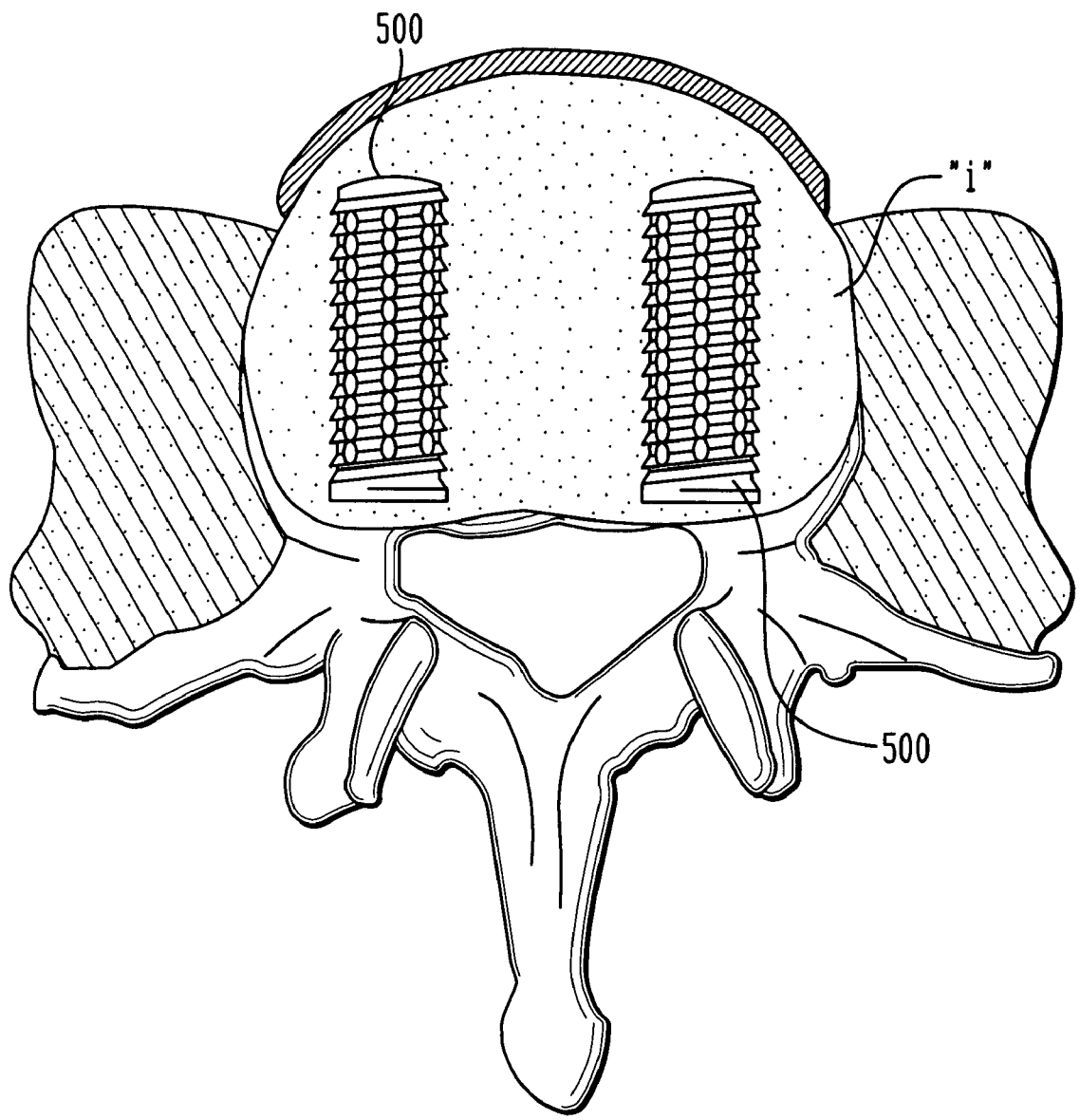
FIG. 7 is a top cross-sectional view of the intervertebral space illustrating insertion of a pair of fusion implants into the intervertebral space.

FIG. 7 illustrates two lateral fusion implants 500 inserted within the intervertebral space. The second fusion cage 500 may be inserted in accordance with the method and instruments previously discussed. After insertion of a first retractor 20 in the first lateral side of the intervertebral space, the first retractor may be left therein to stabilize the intervertebral space while performing implant insertion procedure in the second lateral side of the intervertebral space using the instrumentation above discussed. Then, the first lateral side can be revisited to perform similar implant insertion procedure for implantation of the second fusion cage 500.

While the above description contains many specifics, these specifics should not be construed as limitations on the scope of the disclosure, but merely as exemplifications of preferred embodiments thereof. For example, it is envisioned that a self-tapping implant may be utilized thus precluding the use of tap instrument 300. Those skilled in the art will envision many other possible variations that are within the scope and spirit of the disclosure as defined by the claims appended hereto.

What is claimed is:

1. A system for facilitating insertion of an implant into an intervertebral space, which comprises:
    a retractor including an insertion end portion and a trailing end portion, the insertion end portion configured to at least partially span the intervertebral space defined between adjacent vertebrae to maintain the adjacent vertebrae in a predetermined spaced relation, the retractor defining an internal passage to permit introduction of a surgical instrument therethrough; and
    a guide for guiding the surgical instrument through the internal passage of the retractor, the guide including a guide shaft connectable to the retractor and defining a longitudinal axis and a guide attachment mounted to the guide shaft, the guide attachment adapted for reciprocal longitudinal movement relative to the guide shaft and having mounting structure configured for releasably engaging the surgical instrument such that the surgical instrument is guided along the guide shaft upon longitudinal movement of the guide attachment for reception within the internal passage of the retractor.

2. The system according to claim 1 wherein the guide attachment includes a base defining a longitudinal opening therethrough for receiving the surgical instrument.

3. The system according to claim 2 wherein the base of the guide attachment is configured and dimensioned to receive a surgical drill within the longitudinal opening thereof.

4. The system according to claim 2 wherein the base of the guide attachment is configured and dimensioned to receive an implant insertion instrument within the longitudinal opening thereof.

5. The system according to claim 2 wherein the guide shaft and the guide attachment include corresponding longitudinal guide structure to permit sliding movement along the longitudinal axis without rotational movement therebetween.

6. The system according to claim 1 wherein the guide shaft is releasably connected to the retractor.

7. The system according to claim 1 wherein the retractor includes at least one distractor arm having first and second opposed supporting surfaces for engaging respective opposed vertebrae, the one distractor arm defining a dimension between the first and second supporting surfaces sufficient to maintain the adjacent vertebrae in the predetermined spaced relation.

8. The system according to claim 1 wherein the guide shaft includes a depth indicator for indicating insertion depth of the surgical instrument into the intervertebral space.

9. A method for performing a surgical procedure comprising the steps of:
    introducing a retractor into an intervertebral space defined between adjacent vertebra to maintain the adjacent vertebrae in predetermined space relation, the retractor defining an internal lumen for passage of a surgical instrument and having a longitudinal guide bar releasably connected to the retractor;
    mounting a guide attachment to the guide bar, the guide attachment supporting a surgical instrument;
    advancing the surgical instrument along the guide bar whereby the guide bar guides the surgical instrument through the internal lumen of the retractor and adjacent the intevertebral space, wherein the step of advancing includes sliding the guide attachment along the guide bar whereby the surgical instrument moves with the guide attachment adjacent the intevertebral space; and
    performing a surgical procedure.

10. The method according to claim 9 wherein the surgical instrument is a surgical drill, and the step of performing includes drilling a bore within the intervertebral space.

11. The method according to claim 10 wherein the step of performing includes introducing an implant within the bore of the intervertebral space.

12. The method according to claim 11 wherein the surgical instrument is an implant insertion instrument to which the implant is releasably mounted and wherein the step of introducing the implant includes releasing the implant from the insertion instrument.

13. The method according to claim 9 further including the step of connecting the guide bar to the retractor.

* * * * *